United States Patent
Baik et al.

(10) Patent No.: US 10,512,654 B2
(45) Date of Patent: Dec. 24, 2019

(54) PHARMACEUTICAL COMPOSITION INCLUDING DUTASTERIDE AND CAPSULE FORMULATION COMPRISING THE SAME

(71) Applicant: YUYU PHARMA, INC., Jecheon-si (KR)

(72) Inventors: Taegon Baik, Seoul (KR); Seyeon Kim, Suwon-si (KR); Kyeongjin Ahn, Seoul (KR); Ju-Hee Kim, Suwon-si (KR); Young-joon Park, Gwacheon-si (KR)

(73) Assignee: YUYU PHARMA, INC., Jecheon-si, Chungcheongbuk-do (KR)

( * ) Notice: Subject to any disclaimer, the term of this patent is extended or adjusted under 35 U.S.C. 154(b) by 0 days.

(21) Appl. No.: 15/759,137

(22) PCT Filed: Sep. 9, 2016

(86) PCT No.: PCT/KR2016/010159
§ 371 (c)(1),
(2) Date: Mar. 9, 2018

(87) PCT Pub. No.: WO2017/043913
PCT Pub. Date: Mar. 16, 2017

(65) Prior Publication Data
US 2019/0054094 A1    Feb. 21, 2019

(30) Foreign Application Priority Data

Sep. 10, 2015  (KR) .................. 10-2015-0128264
Dec. 3, 2015   (KR) .................. 10-2015-0171593

(51) Int. Cl.
| | | |
|---|---|---|
| A61K 31/58 | (2006.01) | |
| A61K 9/48 | (2006.01) | |
| A61K 47/14 | (2017.01) | |
| A61K 47/44 | (2017.01) | |
| A61K 47/10 | (2017.01) | |

(52) U.S. Cl.
CPC ............ A61K 31/58 (2013.01); A61K 9/4858 (2013.01); A61K 9/4866 (2013.01); A61K 47/10 (2013.01); A61K 47/14 (2013.01); A61K 47/44 (2013.01)

(58) Field of Classification Search
CPC ........ A61K 31/58; A61K 47/14; A61K 47/44; A61K 9/4858; A61K 47/10
See application file for complete search history.

(56) References Cited

U.S. PATENT DOCUMENTS

| | | | |
|---|---|---|---|
| 2011/0039814 A1* | 2/2011 | Huatan ................ | A61K 9/4858 514/180 |
| 2011/0160168 A1* | 6/2011 | Dhingra ................ | A61K 9/107 514/170 |

FOREIGN PATENT DOCUMENTS

| | | |
|---|---|---|
| CN | 104146966 A | 11/2014 |
| JP | 2002522379 A | 7/2002 |
| KR | 102013008655 A | 8/2013 |
| KR | 101432466 B1 | 8/2014 |
| WO | WO2006113505 A2 | 10/2006 |
| WO | WO2010092596 A1 | 8/2010 |
| WO | WO2012076516 A1 | 6/2012 |
| WO | WO2017116190 A1 | 7/2017 |
| WO | WO2017196148 A1 | 11/2017 |

OTHER PUBLICATIONS

Choo GH, et al."Formulation and in vivo Evaluation of a Self-Microemulsifying Drug Delivery System of Dutasteride", Drug Res. 2013 vol.63. No. 4: 203-209.
European Search Report Issued for EP Application No. 16844729.0 dated Mar. 1, 2019.

* cited by examiner

*Primary Examiner* — Sarah Pihonak
*Assistant Examiner* — Jason Deck

(57) ABSTRACT

The present disclosure relates to a pharmaceutical composition comprising dutasteride and propylene glycol monolaurate, and a capsule formulation comprising the same.

12 Claims, 1 Drawing Sheet

[Fig. 1]
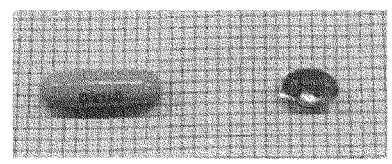
[Fig. 2]
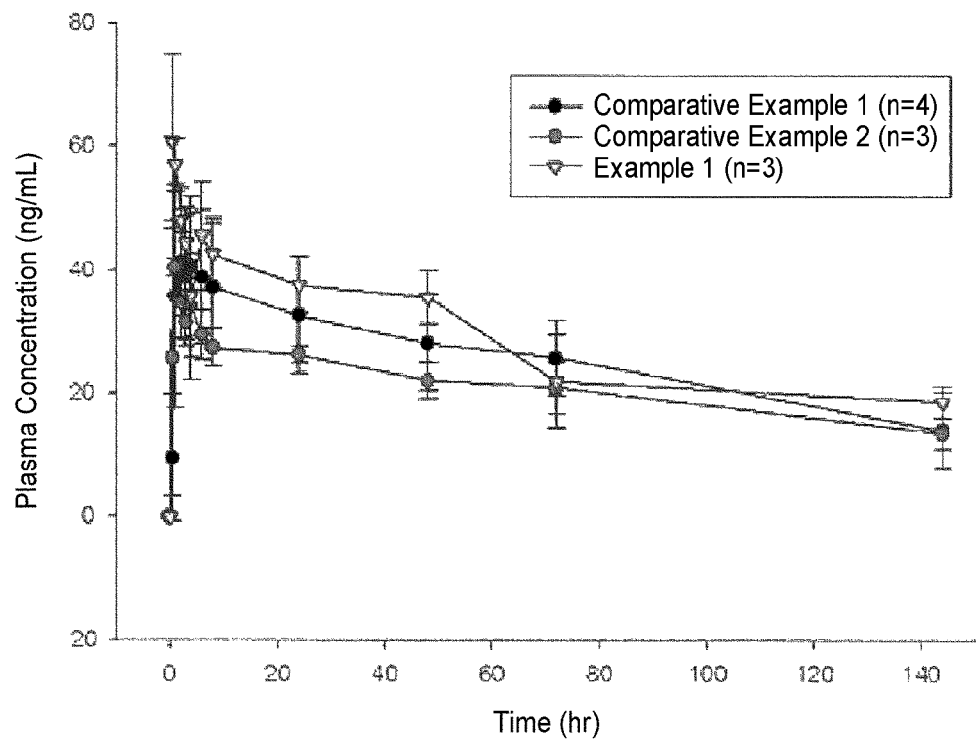

PHARMACEUTICAL COMPOSITION INCLUDING DUTASTERIDE AND CAPSULE FORMULATION COMPRISING THE SAME

TECHNICAL FIELD

The present disclosure relates to a pharmaceutical composition comprising dutasteride, and a capsule formulation comprising the same.

BACKGROUND ART

U.S. Pat. No. 5,565,467 discloses that dutasteride (chemical name: 17β-N-(2,5-bis(trifluoromethyl))phenylcarbamoyl-4-aza-5α-androst-1-en-3-one) of the following Formula (I), a 5-alpha reductase inhibitor, is capable of being used in treating benign prostate hyperplasia, prostate cancer and male pattern alopecia (androgenetic alopecia).

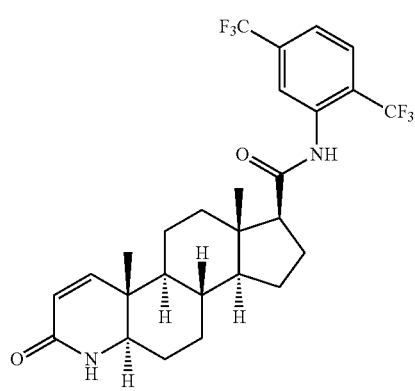

<Formula (I)>

Dutasteride is commercially available as AVODART® soft gelatin capsule which contains 0.5 mg of dutasteride dissolved in 349.5 mg of a mixture of mono- and di-glyceride of caprylic/capric acid and butylated hydroxy toluene (BHT).

However, in order to fill the active ingredient, dutasteride into the soft gelatin capsule, a large amount of oils and surfactants are required to be used, leading to an increase in the size of the capsule. The large-sized capsule may cause low patient compliance due to patient's inability or unwillingness to swallow the large-sized formulations. In particular, considering that the great majority of benign prostate hyperplasia patients is elderly patients, the large size of the dutasteride capsule leads to disadvantages in that taking such large capsule is very inconvenient for elderly patients and thus patient compliance is low.

DISCLOSURE OF INVENTION

Technical Problem

To solve this problem, the present disclosure provides a pharmaceutical composition containing dutasteride having improved stability, patient compliance, dissolution rate and bioavailability, and a capsule formulation comprising the same.

Aspects of the present disclosure are not limited to the technical problem described above, and other technical problems that are not described will be clear to those skilled in the art from the description provided below.

Solution to Problem

In one aspect, the present disclosure relates to a pharmaceutical composition comprising dutasteride of the following Formula (I) and propylene glycol monolaurate:

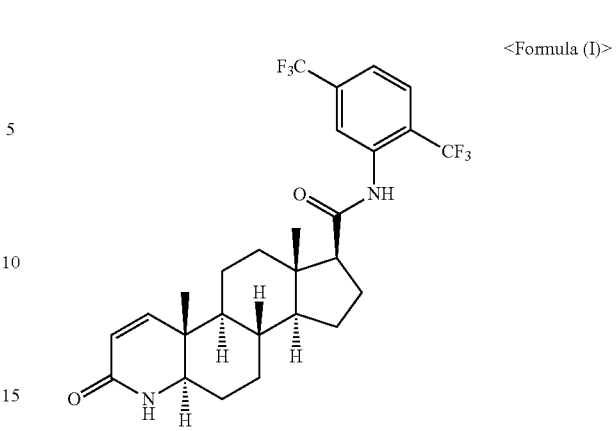

<Formula (I)>

In another aspect of the present disclosure, the pharmaceutical composition further comprises a surfactant having a hydrophile-lypophile balance (HLB) value of greater than or equal to 10 and less than or equal to 30.

According to one embodiment of the present pharmaceutical composition, the content of dutasteride is greater than or equal to 0.1% by weight and less than or equal to 3.0% by weight, the content of propylene glycol monolaurate is greater than or equal to 84.0% by weight and less than or equal to 99.8% by weight, and the content of the surfactant having a HLB value of greater than or equal to 10 and less than or equal to 30 is greater than or equal to 0.1% by weight and less than or equal to 15.0% by weight based on the total weight of the pharmaceutical composition.

According to another embodiment of the present pharmaceutical composition, the surfactant having a HLB value of greater than or equal to 10 and less than or equal to 30 is selected from the group consisting of polyoxyl castor oil, polyoxyl sorbitan fatty acid ester, polyoxyl stearic acid, polyoxyl glyceride, a polyoxyethylene-polyoxypropylene copolymer and any combination thereof.

According to another embodiment of the present pharmaceutical composition, the pharmaceutical composition further comprises one or more of a second surfactant having a hydrophile-lypophile balance (HLB) value of greater than or equal to 6 and less than or equal to 9, and a co-surfactant.

According to another embodiment of the present pharmaceutical composition, the pharmaceutical composition further comprises pharmaceutically acceptable excipients.

In another aspect, the present disclosure relates to a capsule formulation comprising the pharmaceutical composition.

According to one embodiment of the present capsule formulation, the pharmaceutical composition is a clear solution which can be self-emulsified when digested or contact with water.

Other embodiments of the present disclosure are included in the detailed description and the drawings.

Advantageous Effects of Invention

The present disclosure is capable of providing a pharmaceutical composition comprising dutasteride having improved stability, patient compliance, dissolution rate and bioavailability, and a capsule formulation including the same.

Effects of the present disclosure are not limited to the effects illustrated above, and more various effects are included in the present specification.

BRIEF DESCRIPTION OF DRAWINGS

FIG. 1 is a picture comparing a capsule prepared according to one embodiment of the present disclosure and a commercially-available AVODART® capsule.

FIG. 2 is a graph of bioavailability comparison tests of comparative examples and an example of the present disclosure.

MODE FOR THE INVENTION

Advantages and characteristics of the present disclosure, and methods of accomplishing the same may be understood more readily by reference to the following detailed description of embodiments. However, the present disclosure may be embodied in many different forms, and should not be construed as being limited to the embodiments set forth herein. Rather, these embodiments are provided so that this disclosure is thorough and complete and fully conveys the concept of the invention to those skilled in the art, and the present disclosure is only defined by the scope of the appended claims.

In the present specification, a singular form also includes a plural form unless particularly mentioned otherwise in the sentence, and "comprise(s)" and/or "comprising" do not exclude the presence or addition of one or more other constituents.

A pharmaceutical composition according to one embodiment of the present disclosure comprises dutasteride of the following Formula (I) and propylene glycol monolaurate.

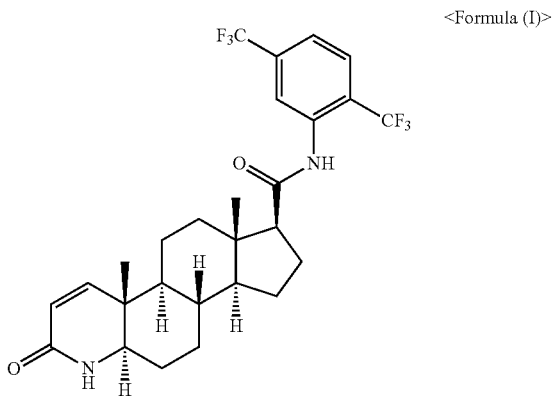

<Formula (I)>

The pharmaceutical composition according to one embodiment of the present disclosure may further comprise a surfactant.

In the present pharmaceutical composition, propylene glycol monolaurate and a surfactant may perform as a solubilizer which solubilizes dutasteride that is a pharmaceutically active ingredient and has poor solubility, and increases its solubility.

The pharmaceutical composition according to one embodiment of the present disclosure is a clear solution which can be self-emulsified when digested or contact with water.

In the pharmaceutical composition according to one embodiment of the present disclosure, the solubility of dutasteride may be increased by using propylene glycol monolaurate or a mixture of propylene glycol monolaurate and a surfactant as a solubilizer of dutasteride.

As a result, the size of the capsule formulation according to one embodiment of the present disclosure becomes smaller compared to AVODART® and is capable of improving patient compliance compared to AVODART®, and improving dissolution rate and bioavailability. FIG. 1 is a picture comparing a capsule prepared according to one embodiment of the present disclosure and a commercially-available AVODART® capsule. When referring to FIG. 1, it is identified that the capsule formulation according to one embodiment of the present disclosure (right, size of 2 oval) is smaller than the AVODART® capsule (left, size of 6 oblong).

Besides, propylene glycol monolaurate is capable of improving the stability of the pharmaceutical composition according to one embodiment of the present disclosure.

Hereinafter, the pharmaceutical composition according to one embodiment of the present disclosure will be described in detail with reference to examples and comparative examples.

Propylene glycol monolaurate is favorably mixed with a surfactant and increases the solubility of dutasteride, and therefore, may form a stable emulsion in water. In addition, propylene glycol monolaurate may enhance the stability of dutasteride.

Test Example 1 is a test result comparing the solubility of dutasteride depending on the types of oil. As identified in Table 1 of Test Example 1, dutasteride is not favorably soluble in general oil such as soybean oil and castor oil, whereas in propylene glycol monolaurate used in the present disclosure, the solubility of dutasteride is higher by 10 times or greater compared to the solubility in general oil.

As shown in Test Examples 2 and 3, the stability of dutasteride in oil was measured by determining whether degradation products are generated when stored under an accelerated stress condition (40° C., 75% RH) and when stored under a stress condition (50° C., 95% RH). When using caprylic/capric acid mono- and di-glyceride oil used in a commercially available AVODART® capsule, many degradation products were generated under both the accelerated and stress conditions. However, degradation products were not generated in propylene glycol monolaurate oil when stored under an accelerated condition for 4 weeks. Further, even when stored under a stress condition for 4 weeks, it was seen that significantly smaller amounts of degradation products were produced compared to caprylic/capric acid mono- and di-glyceride.

In addition, as identified in a stability test (Test Example 3), a mixture of propylene glycol monocaprylate with a surfactant shows favorable solubility for dutasteride, but significantly low stability of dutasteride. However, it was identified that both solubility and stability of dutasteride was very superior in a mixture of propylene glycol monolaurate with a surfactant.

Based on the solubility and stability tests, it was identified that propylene glycol monolaurate is capable of enhancing solubility and stability of dutasteride in the pharmaceutical composition of the present disclosure.

Meanwhile, the surfactant of the present disclosure performs a role of enhancing the solubility of dutasteride and forming a stable emulsion by stably emulsifying propylene glycol monolaurate in water. The surfactant of the present disclosure may comprise a first surfactant having a hydrophile-lypophile balance (HLB) value of greater than or equal to 10 and less than or equal to 30, and optionally one or more of a second surfactant having a HLB value of greater than or equal to 6 and less than or equal to 9 and a co-surfactant.

For example, the surfactant may be the first surfactant, or a mixture of the first surfactant and the second surfactant, or a mixture of the first surfactant and the co-surfactant. The second surfactant may perform a role of maintaining stability in water by assisting solubilization of dutasteride, and the co-surfactant may perform a role of assisting solubilization of dutasteride. The second surfactant and the co-surfactant are supplements assisting the role of the first surfactant, and the surfactant essentially consists of the first surfactant.

In this regard, according to the results of phase equilibrium study, when using, for example, a mixture comprising polyoxyl 40 hydrogenated castor oil and poloxamer 124 as the surfactant, the mixture of polyoxyl 40 hydrogenated castor oil and poloxamer 124 were well blended with propylene glycol monolaurate, thereby forming a stable emulsion in water.

Examples of the first surfactant may include one or more of polyoxyl castor oil, polyoxyl sorbitan fatty acid ester, polyoxyl stearic acid, polyoxyl glyceride and a poly-oxyethylene-polyoxypropylene copolymer, including, but not limited to, poly-oxyethylene 35 castor oil, polyethylene glycol (PEG) 6 glyceryl caprylate/caprate, PEG 40 hydrogenated castor oil, poloxamer 124, poloxamer 188, and PEG 15 hydroxystearate. Examples of the second surfactant may include, but not limited to, sorbitan fatty acid ester, for example, polysorbate 80, polysorbate 60, and polysorbate 40. Examples of the co-surfactant may include, but not limited to, diethylene glycol monoethyl ether, propylene glycol, polyethylene glycol and the like, for example, Transcutol, PEG 600, and PEG 300.

When the pharmaceutical composition according to one embodiment of the present disclosure includes dutasteride, propylene glycol monolaurate and a surfactant, the dutasteride content may be greater than or equal to 0.1% by weight and less than or equal to 3.0% by weight based on the total weight of the pharmaceutical composition, and the propylene glycol monolaurate content may be greater than or equal to 84.0% by weight and less than or equal to 99.8% by weight based on the total weight of the pharmaceutical composition, and the surfactant content may be greater than or equal to 0.1% by weight and less than or equal to 15.0% by weight based on the total weight of the pharmaceutical composition.

The content of dutasteride may be 0.1 to 3.0% by weight, preferably 0.1 to 1.0% by weight, more preferably 0.2 to 0.6% by weight based on the total weight of the pharmaceutical composition. When the dutasteride content is less than 0.1% by weight based on the total weight of the pharmaceutical composition, the solubilizer content relatively increases, thereby leading to an increase in the mass of the capsule, which is disadvantageous in that taking the medicine is inconvenient. The dutasteride content of greater than 3.0% by weight based on the total weight of the pharmaceutical composition is disadvantageous in that it is difficult to dissolve dutasteride.

The content of propylene glycol monolaurate may be 84.0 to 99.8% by weight, preferably 90.0 to 99.0% by weight, more preferably 95.0 to 98.0% by weight based on the total weight of the pharmaceutical composition. When the propylene glycol monolaurate content is less than 84.0% by weight based on the total weight of the pharmaceutical composition, dutasteride is not sufficiently dissolved, which may lead to a disadvantage of precipitation. When the propylene glycol monolaurate content is greater than 99.8% by weight based on the total weight of the pharmaceutical composition, the amount of the surfactant used decreases, which may cause decline in the emulsifying ability of the formulation.

The content of the first surfactant may be greater 0.1 to 15.0% by weight, preferably 1.0 to 10% by weight, more preferably 2.0 to 5.0% by weight based on the total weight of the pharmaceutical composition. When the first surfactant content is less than 0.1% by weight based on the total weight of the pharmaceutical composition, the emulsion forming ability may decline. When the first surfactant content is greater than 15.0% by weight based on the total weight of the pharmaceutical composition, the capsule is hardened and may cause decline in the stability of the formulation and the stability of dutasteride.

Meanwhile, the pharmaceutical composition according to one embodiment of the present disclosure may further comprise pharmaceutically acceptable excipients within the scope that does not interfere with the purpose of the present disclosure. The pharmaceutically acceptable excipients may be selected from one or more of antioxidants, colorants, and preservatives. Examples of the antioxidants may include butylated hydroxy toluene (BHT), butylated hydroxy anisole (BHA) and the like.

The pharmaceutical composition according to one embodiment of the present disclosure may be prepared by uniformly mixing dutasteride, propylene glycol monolaurate and a surfactant.

The capsule formulation according to one embodiment of the present disclosure may be a soft capsule formulation or a hard capsule formulation, and may be prepared by filling the soft capsule base or the hard capsule base with a homogeneously mixed solution of dutasteride, propylene glycol monolaurate and a surfactant according to a method for preparing a capsule formulation known in the art.

The amount of the mixed solution of dutasteride, propylene glycol monolaurate and a surfactant being filled in a capsule formulation can be 92 mg to 185 mg, preferably 100 mg to 150 mg, more preferably 110 mg. The capsule formulation of the present disclosure can be prepared in size 2 oval (minims: 1.5-1.8, cc: 0.092-0.111), size 3 oval (minims: 2.4-3.0, cc: 0.148-0.185), size 3 oblong (minims: 2.3-3.0, cc: 0.142-0.185), size 4 oblong (minims: 3.0-4.0, cc: 0.185-0.246) and the like. The size of the capsule formulation according to one embodiment of the present disclosure is smaller compared to size 6 oblong of AVODART® (minims: 5.0-6.0, cc: 0.308-0.370). Thus, the capsule formulation of the present disclosure is capable of improving patient compliance compared to AVODART®.

The following test examples indicate that the pharmaceutical composition according to one embodiment of the present disclosure and a capsule formulation including the same exhibit excellent stability, excellent patient compliance, excellent dissolution rate, excellent bioavailability and the like compared to comparative examples.

Hereinafter, the present disclosure will be described in detail with reference to examples so that those having average knowledge in the technology field to which the present disclosure belongs may readily carry out the invention. However, the present disclosure may be embodied in various different forms and is not limited to the examples described herein.

Example 1

To a 3 L preparation container equipped with a stirrer, 1,040 g of propylene glycol monolaurate was added, and while stirring, 5 g of dutasteride was slowly added thereto and completely dissolved. 33 g of polyoxyl 40 hydrogenated castor oil and 22 g of poloxamer 124 were added thereto, and the resultant mixture was stirred to prepare a solubilized composition. A soft capsule shell was prepared using gelatin, a plasticizer and the like according to a method known in the art. After filling a size 2 oval soft capsule with 110 mg of the prepared solubilized composition using a rotary-type automatic filler, a soft capsule formulation for oral administration was prepared after going through drying and sorting processes.

Examples 2 to 8

To a 500 mL preparation container equipped with a stirrer, 104 g of propylene glycol monolaurate was added, and while stirring, 0.5 g of dutasteride was slowly added thereto and completely dissolved. Surfactants were added thereto in the amounts specified in the following Table 1, and after stirring and thoroughly mixing the resultant mixture, 0.01 g of butylated hydroxy toluene was added thereto and dissolved to prepare a solubilized composition. A soft capsule shell was prepared using a method known in the art as in Example 1. After filling a size 2 oval soft capsule with 110 mg of the prepared solubilized composition using a rotary-type automatic filler, a soft capsule formulation for oral administration was prepared after going through drying and sorting processes.

TABLE 1

| Content | Example 2 | Example 3 | Example 4 | Example 5 | Example 6 | Example 7 | Example 8 |
|---|---|---|---|---|---|---|---|
| Dutasteride | 0.5 g | 0.5 g | 0.5 g | 0.5 g | 0.5 g | 0.5 g | 0.5 g |
| Propylene Glycol Monolaurate | 104 g | 104 g | 104 g | 104 g | 104 g | 104 g | 104 g |
| Butylated Hydroxy Toluene | 0.01 g | 0.01 g | 0.01 g | 0.01 g | 0.01 g | 0.01 g | 0.01 g |
| Polyoxyethylene 35 Castor Oil | 5.49 g | | | | | 3.3 g | |
| PEG 40 Hydrogenated Castor Oil | | 5.49 g | | | | | 3.3 g |
| Polysorbate 80 | | | 5.49 g | | | | |
| PEG 6 Glyceryl Carpylate/Caprate | | | | 5.49 g | | | |
| PEG 15 Hydroxystearate | | | | | 5.49 g | | |
| Poloxamer 124 | | | | | | 2.19 g | 2.19 g |

Examples 9 to 15

To a 500 mL preparation container equipped with a stirrer, propylene glycol monolaurate was added in the amount specified in the following Table 2, and while stirring, 0.5 g of dutasteride was slowly added thereto and completely dissolved. Surfactants were added thereto in the amounts specified in the following Table 2, and after stirring and thoroughly mixing the resultant mixture, butylated hydroxy toluene was added thereto and dissolved to prepare a solubilized composition. A soft capsule shell was prepared in the same manner as in Example 1. After filling a size 2 oval soft capsule with 110 mg of the prepared solubilized composition using a rotary-type automatic filler, a soft capsule formulation for oral administration was prepared after going through drying and sorting processes.

glycol dicaprylate, propylene glycol dicaprate and propylene glycol monolaurate was measured. In a 10 mL vial, a magnetic bar was placed. After 3 mL of the oil was added thereto, approximately 100 mg of dutasteride was added thereto while stirring under a room temperature (25° C.) condition, and the resultant mixture was stirred with 500 rpm or higher. After stirring for 24 hours, 1 mL of the resultant mixture was taken and separated using a centrifuge, and only the supernatant was taken to quantify the amount of dutasteride dissolved in the oil using liquid chromatography. As for the solubility in each oil obtained from the test results, propylene glycol monolaurate exhibited higher solubility by 10 times or greater compared to other tested oils, as shown in Table 3.

TABLE 2

| Content | Example 9 | Example 10 | Example 11 | Example 12 | Example 13 | Example 14 | Example 15 |
|---|---|---|---|---|---|---|---|
| Dutasteride | 0.5 g | 0.5 g | 0.5 g | 0.5 g | 0.5 g | 0.5 g | 0.5 g |
| Propylene Glycol Monolaurate | 106 g | 105 g | 104 g | 106 g | 108 g | 105 g | 105 g |
| Butylated Hydroxy Toluene | 0.01 g | 0.01 g | 0.01 g | 0.01 g | 0.01 g | 0.01 g | 0.01 g |
| Polyoxyethylene 35 Castor Oil | 3.49 g | — | — | — | 1.3 g | 2.3 g | 2.3 g |
| PEG 40 Hydrogenated Castor Oil | — | 4.49 g | — | — | — | — | — |
| PEG 6 Glyceryl Carpylate/Caprate | — | — | 2.49 g | — | — | — | — |
| PEG 15 Hydroxystearate | — | — | — | 3.49 g | — | — | — |
| Poloxamer 124 | — | — | 3 g | — | 0.19 g | — | — |
| Poloxamer 188 | — | — | — | — | — | 2.19 g | — |
| Transcutol | — | — | — | — | — | — | 2.19 g |

Example 16

To a 0.5 L preparation container equipped with a stirrer, 104 g of propylene glycol monolaurate was added, and while stirring, 0.5 g of dutasteride was slowly added thereto and completely dissolved. 33 g of polyoxyl 40 hydrogenated castor oil and 22 g of lecithin were added thereto, and the resultant mixture was stirred to prepare a solubilized composition. A size 4 oblong gelatin hard capsule was filled with 110 mg of the solubilizer composition to prepare a hard capsule formulation for oral administration.

Test Example 11

In order to measure the solubility of dutasteride in oil, the solubility of dutasteride in soybean oil, castor oil, propylene

TABLE 3

Solubility of Dutasteride Depending on Oil Type

| Oil | Solubility of Dutasteride (mg/mL) |
|---|---|
| Soybean Oil | 0.00 |
| Castor Oil | 1.50 |
| Propylene Glycol Dicaprylate | 1.13 |
| Propylene Glycol Dicaprate | 0.77 |
| Propylene Glycol Monolaurate | 10.43 |

Test Example 2: Test I on Stability of Pharmaceutical Composition Depending on Oil Type In order to identify the stability of dutasteride in propylene glycol monolaurate exhibiting the excellent solubility in the solubility evaluation, the stability of dutasteride in mono-di-glyceride of caprylic/capric acid used as an oil phase of AVODART®, an existing commercially-available formulation, was compared under a stress condition (50° C., 95% RH) and an accelerated condition (40° C. 75% RH). As samples used in the comparison test, a sample dissolving 1.0 mg of dutasteride in 10.0 mg of propylene glycol monolaurate and stored in a transparent vial, and a sample dissolving 1.0 mg of dutasteride in 10.0 mg of caprylic/capric acid mono-di-glyceride and stored in a transparent vial were used. The percentage of degradation products with respect to dutasteride, a main substance, was calculated and summarized in the following Table 4.

TABLE 4

Evaluation I on Stability of Dutasteride Depending on Oil Type

| Oil | Storage Condition | Amount of Degradation Products (%) After 4 Weeks |
|---|---|---|
| Propylene Glycol Monolaurate | Accelerated Condition (40° C., 75% RH) | None |
|  | Stress Condition (50° C., 95% RH) | 0.32% |
| Caprylic/Capric Acid Mono-Di-Glyceride | Accelerated Condition (40° C., 75% RH) | 0.94% |
|  | Stress Condition (50° C., 95% RH) | 1.75% |

As can be identified from Table 4, the stability of dutasteride in propylene glycol monolaurate was more superior compared to the caprylic/capric acid mono-di-glyceride in the week 4 under an accelerated condition (40° C., 75% RH) and a stress condition (50° C., 95% RH).

Test Example 3

A stability test on the pharmaceutical composition of the comparative example dissolving 0.5 mg of dutasteride in a mixture of 95 mg of propylene glycol monocaprylate and 5 mg of polyoxyl 35 castor oil and stored in a transparent vial, and the pharmaceutical composition of the example including dutasteride, propylene glycol monolaurate and polyoxyl 35 castor oil was carried out by identifying the generation of degradation products under an accelerated condition (40° C., 75% RH) and a stress condition (50° C. 95% RH). As shown in the following Table 5, it was seen that the mixture of propylene glycol monolaurate and a surfactant secured the stability of dutasteride unlike mixtures of surfactant with other oils such as propylene glycol monocaprylate.

TABLE 5

Evaluation II on Stability of Dutasteride in Mixture of Oil and Surfactant

| Oil | Surfactant | Amount of Degradation Products (%) | |
|---|---|---|---|
|  |  | After 3 Weeks | After 4 Weeks |
| Propylene Glycol Monolaurate | Polyoxyl 35 Castor Oil | None | None |
| Propylene Glycol Monocaprylate | Polyoxyl 35 Castor Oil | 6.2% | 12.1% |

Test Example 4: Stress Test on Stability in Soft Capsule

In order to evaluate the stability in a soft capsule formulation, the soft capsule formulation of Example 1 was transparent PVDC blister packed, and then each stored under each of various stress conditions (light: 300 W/m$^2$, temperature: 50° C., or humidity: 95% RH) to identify the presence of degradation products.

TABLE 6

Results of Stress Test on Stability in Soft Capsule Formulation

| | Condition | | |
|---|---|---|---|
| | Light: 300 W/m$^2$ | Temperature: 50° C. | Humidity: 95% RH |
| Example 1 | 6 Hours: None 3 Days: None | 1 Week: None 2 Weeks: None 3 Weeks: None 4 Weeks: None | 1 Week: None 2 Weeks: None 3 Weeks: None 4 Weeks: None |

Test Example 5: In Vivo Bioavailability Comparison Test on Beagle Dog

A bioavailability comparative evaluation in beagle dogs was carried out using Example 1, Comparative Example 1 and Comparative Example 2. Beagle dogs were used as the in vivo test animal. Four beagle dogs were used for Comparative Example 1, a commercially-available formulation, and three beagle dogs were used each for Example 1 and Comparative Example 2. 0.5 mg of dutasteride and 40 mL of drinking water were orally administered to each beagle dogs starved in advance.

After the oral administration, blood was collected at times after 0 hours, 0.5 hours, 1 hour, 2 hours, 3 hours, 4 hours, 6 hours, 8 hours, 24 hours, 48 hours, 72 hours and 144 hours had passed, and the concentrations of dutasteride in the blood were analyzed using HPLC/Ms/Ms.

As Comparative Example 1, a currently commercially-available AVODART® 0.5 mg soft capsule containing 0.5 mg of dutasteride was used. As Comparative Example 2, a soft capsule was prepared so as to contain 0.5 mg of dutasteride per 1 capsule as in Example 1 except that the solubilized composition was prepared by placing and dissolving 0.5 g of dutasteride in 104 g of propylene monocaprylate, 3.3 g of polyoxyl 35 castor oil and 2.19 g of poloxamer 124 while stirring.

As can be identified in the following Table 7 and FIG. 2, Example 1 had more improved bioavailability compared to Comparative Example 1 and Comparative Example 2. Particularly, Example 1 had a smaller formulation size, but exhibited improved bioavailability compared to AVODART® of Comparative Example 1.

TABLE 7

| | Results of in vivo Bioavailability Test on Beagle Dog | | |
|---|---|---|---|
| | $AUC_t$ (ng/mL × hr)[1] | $C_{max}$ (ng/mL)[2] | $T_{max}$ (hr)[3] |
| Example 1 | 4020.90 ± 702.78 | 63.04 ± 10.77 | 0.67 ± 0.29 |
| Comparative Example 1 | 3654.08 ± 753.09 | 47.08 ± 8.39 | 3.25 ± 1.50 |
| Comparative Example 2 | 3008.46 ± 62.97 | 41.30 ± 1.92 | 2.00 ± 1.73 |

[1]Area under Curve of Concentration in Blood up to 144 Hours after Administration
[2]Maximum Concentration in Blood
[3]Time at Maximum Concentration in Blood

Test Example 6: Dissolution Test

A dissolution evaluation was carried out on the soft capsule formulation of Example 1 and the commercially-available AVODART® 0.5 mg soft capsule of Comparative Example 1. The dissolution test was carried out in accordance with Method 2 of the dissolution test method in the Korean Pharmacopoeia. 10th edition using a 0.1% aqueous lauryl sodium sulfate solution as the eluent and a rotation speed of 50 rpm. As shown in the following Table 8, it was identified that the dissolution rate in Example 1 was more superior compared to the AVODART® of Comparative Example 1.

TABLE 8

| Result of Evaluation on Dissolution | | |
|---|---|---|
| | Example 1 | Comparative Example 1 |
| 5 Minutes | 26.5% | 0.0% |
| 10 Minutes | 56.1% | 36.4% |
| 15 Minutes | 68.3% | 49.5% |
| 30 Minutes | 87.1% | 55.6% |

The test examples and the like are for illuminating the present disclosure, and technological ideas of the present disclosure are not limited to the test examples and the like described above. Substitution of equivalents, addition or deletion of other constituents, and the like within the scope of not impairing the technological ideas of the present disclosure are still incorporated into the present specification and constitute the contents of the present disclosure.

The invention claimed is:

1. A pharmaceutical composition comprising dutasteride of the following Formula (I), propylene glycol monolaurate, and a surfactant having a hydrophile-lypophile balance (HLB) value of greater than or equal to 10 and less than or equal to 30:

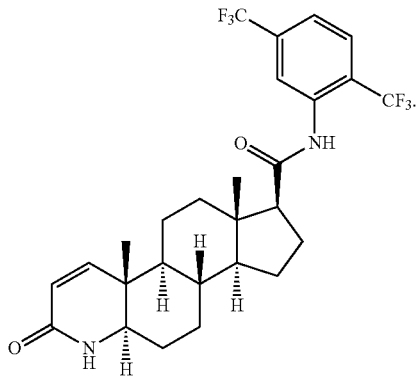

<Formula (I)> wherein a content of dutasteride is greater than or equal to 0.1% by weight and less than or equal to 3.0% by weight,
a content of propylene glycol monolaurate is greater than or equal to 84.0% by weight and less than or equal to 99.8% by weight, and
a content of the surfactant is greater than or equal to 0.1% by weight and less than or equal to 15.0% by weight based on a total weight of the pharmaceutical composition.

2. The pharmaceutical composition of claim 1, wherein the surfactant having a HLB value of greater than or equal to 10 and less than or equal to 30 is selected from the group consisting of polyoxyl castor oil, polyoxyl sorbitan fatty acid ester, polyoxyl stearic acid, polyoxyl glyceride, a polyoxyethylene-polyoxypropylene copolymer and any combination thereof.

3. The pharmaceutical composition of claim 1, further comprising one or more of a second surfactant having a hydrophile-lypophile balance (HLB) value of greater than or equal to 6 and less than or equal to 9, and a co-surfactant.

4. The pharmaceutical composition of claim 1, further comprising pharmaceutically acceptable excipients.

5. A capsule formulation comprising the pharmaceutical composition of claim 1.

6. The capsule formulation of claim 5, wherein the pharmaceutical composition is a clear solution which can be self-emulsified when digested or contact with water.

7. A capsule formulation comprising the pharmaceutical composition of claim 2.

8. The capsule formulation of claim 7, wherein the pharmaceutical composition is a clear solution which can be self-emulsified when digested or contact with water.

9. A capsule formulation comprising the pharmaceutical composition of claim 3.

10. The capsule formulation of claim 9, wherein the pharmaceutical composition is a clear solution which can be self-emulsified when digested or contact with water.

11. A capsule formulation comprising the pharmaceutical composition of claim 4.

12. The capsule formulation of claim 11, wherein the pharmaceutical composition is a clear solution which can be self-emulsified when digested or contact with water.

* * * * *